US009949878B2

(12) United States Patent  
Pawar et al.

(10) Patent No.: US 9,949,878 B2  
(45) Date of Patent: Apr. 24, 2018

(54) SYSTEM AND METHOD TO AUTOMATICALLY SWITCH ON AND SWITCH OFF DEVICE FOR ACCURATE RECORDING OF PERSONAL SOUND EXPOSURE MEASUREMENTS

(71) Applicant: Honeywell International Inc., Morristown, NJ (US)

(72) Inventors: Sunil Bhila Pawar, Bangalore (IN); Trym Holter, Trondheim (NO)

(73) Assignee: Honeywell International Inc., Morris Plains, NJ (US)

(*) Notice: Subject to any disclaimer, the term of this patent is extended or adjusted under 35 U.S.C. 154(b) by 79 days.

(21) Appl. No.: 14/645,114

(22) Filed: Mar. 11, 2015

(65) Prior Publication Data

US 2016/0262940 A1 Sep. 15, 2016

(51) Int. Cl.
*A61F 11/06* (2006.01)
*H04R 1/10* (2006.01)
(Continued)

(52) U.S. Cl.
CPC ............ *A61F 11/08* (2013.01); *H04R 1/1083* (2013.01); *A61F 2011/145* (2013.01); *H04R 2460/01* (2013.01)

(58) Field of Classification Search
CPC .. A61F 11/08; A61F 2011/145; H04R 1/1041; H04R 2460/15
USPC .................................................... 381/72, 74
See application file for complete search history.

(56) References Cited

U.S. PATENT DOCUMENTS

| 5,631,965 A | 5/1997 | Chang et al. |
| 2006/0029234 A1* | 2/2006 | Sargaison ........... H04M 1/6058 381/74 |

(Continued)

FOREIGN PATENT DOCUMENTS

| DE | 4410445 | 9/1995 |
| EP | 0674466 A1 | 9/1995 |

(Continued)

OTHER PUBLICATIONS

International Application No. PCT/US2016/020079, International Search Report, dated May 10, 2016, 4 pages.

(Continued)

*Primary Examiner* — Vivian Chin
*Assistant Examiner* — Ammar Hamid
(74) *Attorney, Agent, or Firm* — Wick Phillips Gould & Martin, LLP (57) ABSTRACT

Embodiments relate generally to an active hearing protection device comprising a communication device operable to provide active hearing protection to a wearer; a set of earmuffs connected to the communication device, wherein each earmuff comprises an indicator mechanism operable to indicate to the communication device when the earmuff is inserted into a user's ear, a processor operable to receive information from the set of earmuffs and the indicator mechanisms of the earmuffs, and operable to automatically power the active hearing protection device on or off based on the information received from the indicator mechanism(s). When it is determined that both earmuffs are inserted into the user's ears, the active hearing protection device is powered on, and when it is determined that at least one of the earmuffs is not inserted into the user's ear(s), the active hearing protection device is powered off.

20 Claims, 5 Drawing Sheets

(51) Int. Cl.
*A61F 11/08* (2006.01)
*A61F 11/14* (2006.01)

(56) References Cited

U.S. PATENT DOCUMENTS

| | | | |
|---|---|---|---|
| 2009/0010464 A1 | 1/2009 | Komagel | |
| 2009/0122996 A1* | 5/2009 | Klein | H04R 29/00 381/56 |
| 2009/0226013 A1* | 9/2009 | Burge | H04R 1/1041 381/309 |
| 2010/0246845 A1 | 9/2010 | Burge et al. | |
| 2014/0321682 A1 | 10/2014 | Kofod-Hansen et al. | |
| 2015/0010158 A1 | 1/2015 | Broadley et al. | |
| 2015/0181325 A1* | 6/2015 | Urup | H04R 1/1091 381/74 |

FOREIGN PATENT DOCUMENTS

| | | |
|---|---|---|
| EP | 2675189 A1 | 12/2013 |
| WO | 2016144592 A1 | 9/2016 |

OTHER PUBLICATIONS

International Application No. PCT/US2016/020079, Written Opinion of the International Searching Authority, dated May 10, 2016, 6 pages.
International Application No. PCT/US2016/020079, International Preliminary Report on Patentability, dated Sep. 12, 2017, 7 pages.

* cited by examiner

SYSTEM AND METHOD TO AUTOMATICALLY SWITCH ON AND SWITCH OFF DEVICE FOR ACCURATE RECORDING OF PERSONAL SOUND EXPOSURE MEASUREMENTS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Active hearing protection devices may actively cancel noises in the environment to protect the hearing of a user, possibly using microphones and speakers to detect the sounds from the environment and then generate a cancelling frequency. Additionally, some active hearing protection devices may comprise communication systems, such as radio systems, allowing a wearer to communicate with other workers, for example. Typical active hearing protection devices may be manually powered on and off by a user. Active hearing protection devices may also collect exposure data while the device is turned on.

SUMMARY

Aspects of the disclosure may include embodiments of an active hearing protection device comprising: a communication device operable to provide active hearing protection to a wearer; a set of earmuffs connected to the communication device, wherein each earmuff comprises an indicator mechanism operable to indicate to the communication device when the earmuff is inserted into a user's ear, a processor operable to receive information from the set of earmuffs and the indicator mechanisms of the earmuffs, and operable to automatically power the active hearing protection device on or off based on the information received from the indicator mechanism(s).

In some embodiments, when it is determined that both earmuffs are inserted into the user's ears, the active hearing protection device is powered on, and when it is determined that at least one of the earmuffs is not inserted into the user's ear(s), the active hearing protection device is powered off. In some embodiments, the communication device comprises a user interface operable to receive input from a user and communicate information to the user, and the user interface comprises a menu button, a power button and a screen; and one or more ports for connecting the earmuffs, radio devices, microphones, and other devices to the communication device. In some embodiments, the information received by the communication device from the earmuffs comprises data related to active hearing protection from the earmuffs, including one or more of the following: noise exposure levels, frequency levels, decibel levels, and time of exposure. In some embodiments, the earmuffs are operable to communicate voice communication to a user received via a radio connection, and wherein the earmuffs may comprise a voice pick-up device operable to pick up the voice of a wearer for communication over the radio connection. In some embodiments, a fit test is performed by the active hearing protection device when the device is turned on, to ensure that the earmuffs are worn correctly and providing adequate hearing protection. In some embodiments, the indication mechanism(s) comprise one or more of the following: a pressure sensor, a push button, a thermal sensor, and an accelerometer. In some embodiments, the indication mechanism comprises a pressure sensor located within an internal portion of the earmuff, and wherein the pressure sensor is compressed when the internal portion of the earmuff is inserted into a wearer's ear canal. In some embodiments, the indication mechanism comprises a push button operable to interact with the surface of a wearer's ear canal.

Additional aspects of the disclosure may include embodiments of an active hearing protection device comprising a communication device operable to provide active hearing protection to a wearer, a set of earmuffs connected to the communication device, wherein each earmuff comprises an indicator mechanism operable to indicate to the communication device when the earmuff is inserted into a user's ear, a processor operable to receive information from the set of earmuffs and the indicator mechanisms of the earmuffs, and operable to automatically power the active hearing protection device on or off based on the information received from the indicator mechanism(s), wherein, when it is determined that both earmuffs are inserted into the user's ears, the active hearing protection device is powered on, and when it is determined that at least one of the earmuffs is not inserted into the user's ear(s), the active hearing protection device is powered off, wherein the information received by the communication device from the earmuffs comprises noise exposure data related to active hearing protection from the earmuffs, and wherein a fit test is performed by the active hearing protection device when the active hearing protection device is turned on, to ensure that the earmuffs are worn correctly and providing adequate hearing protection.

In some embodiments, the indication mechanism comprises a pressure sensor located within an internal portion of the earmuff, and wherein the pressure sensor is compressed when the internal portion of the earmuff is inserted into a wearer's ear canal. In some embodiments, the indication mechanism comprises a push button operable to interact with the surface of a wearer's ear canal. In some embodiments, turning on the active hearing protection device comprises a 10 second delay before the fit test is completed, allowing the earmuffs to expand into the ear canal of the wearer. In some embodiments, turning off the active hearing protection device happens approximately immediately when at least one indicator mechanism indicates that at least one earmuff has been removed from the ear of a wearer.

Other aspects of the disclosure may include embodiments of a method for automatically powering on or off an active hearing protection device comprising receiving, by a processor in the active hearing protection device, information from two earmuffs, wherein the earmuffs are connected to the active hearing protection device; receiving indication from a first indicator mechanism that a first earmuff has been inserted into a user's ear, receiving indication from a second indicator mechanism that a second earmuff has been inserted into a user's ear, powering on the active hearing protection device, after receiving indication from both the first indicator and the second indicator that both the first earmuff and the second earmuff have been inserted into a user's ear, performing a fit test on the first earmuff and the second earmuff after a delay; and receiving noise exposure data from the earmuffs while the active hearing protection device is turned on.

In some embodiments, the method further comprises receiving indication from the first indicator mechanism that the first earmuff has been removed from a user's ear; and powering off the active hearing protection device. In some embodiments, the method further comprises receiving indication from the first indicator mechanism that the first earmuff has been reinserted into a user's ear; powering on the active hearing protection device; performing a fit test on the first earmuff and the second earmuff after a delay; and receiving noise exposure data from the earmuffs while the active hearing protection device is turned on. In some embodiments, the method further comprises receiving indication from the second indicator mechanism that the second earmuff has been removed from a user's ear and powering off the active hearing protection device. In some embodiments, the indication mechanism comprises a pressure sensor located within an internal portion of the earmuff, and wherein the pressure sensor is compressed when the internal portion of the earmuff is inserted into a wearer's ear canal. In some embodiments, the indication mechanism comprises a push button operable to interact with the surface of a wearer's ear canal.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include active hearing protection devices comprising one or more indicator mechanisms for automatically powering on and/or off of the device. Typical active hearing protection devices may require manual powering on or off of the device. For example, a user may hold a power button for a period of time (such as 3 seconds) to power the device on and similarly to power the device off. This requires the user to have free hands and easy access to the device when the user wishes to power the device on or off. Sometimes, a user may power on the device before inserting the earmuffs of the device, resulting in an unnecessary use of battery and inaccurate exposure data collection. Sometimes a user may forget to power off the device, resulting in an unnecessary use of battery and inaccurate exposure data collection. Additionally, if an earmuff is removed and reinserted by a user, the device should be turned off and back on to complete a fit test for the reinserted earmuff. However, sometimes a user may not complete this procedure because of inconvenience, which may result in an inadequate fit of the earmuff.

The current disclosure comprises an active hearing protection device comprising an indicator mechanism location in each of the two earmuffs. The indicator mechanisms indicate to the device whether the earmuffs are inserted into a user's ear or not. The device may automatically power on when both indicator mechanisms indicate that both earmuffs are inserted. The device may then complete a fit test after a delay allowing the earmuffs to expand in the user's ear canal. Similarly, the device may automatically power off if at least one of the indicator mechanisms indicates that at least one of the earmuffs has been removed from (or is not yet inserted into) the ear canal of a user. This may prevent wearing of the device without a correct fit test, prevent wasted battery life, and prevent collection of inaccurate exposure data. Additionally, if an earmuff is removed and reinserted, the device may be automatically powered off with the removal and then automatically powered back on with reinsertion, allowing for a new fit test to be performed on the reinserted earmuff(s). In some embodiments, the active hearing protection device may be known as a Quiet-Pro device.

Figure 1:
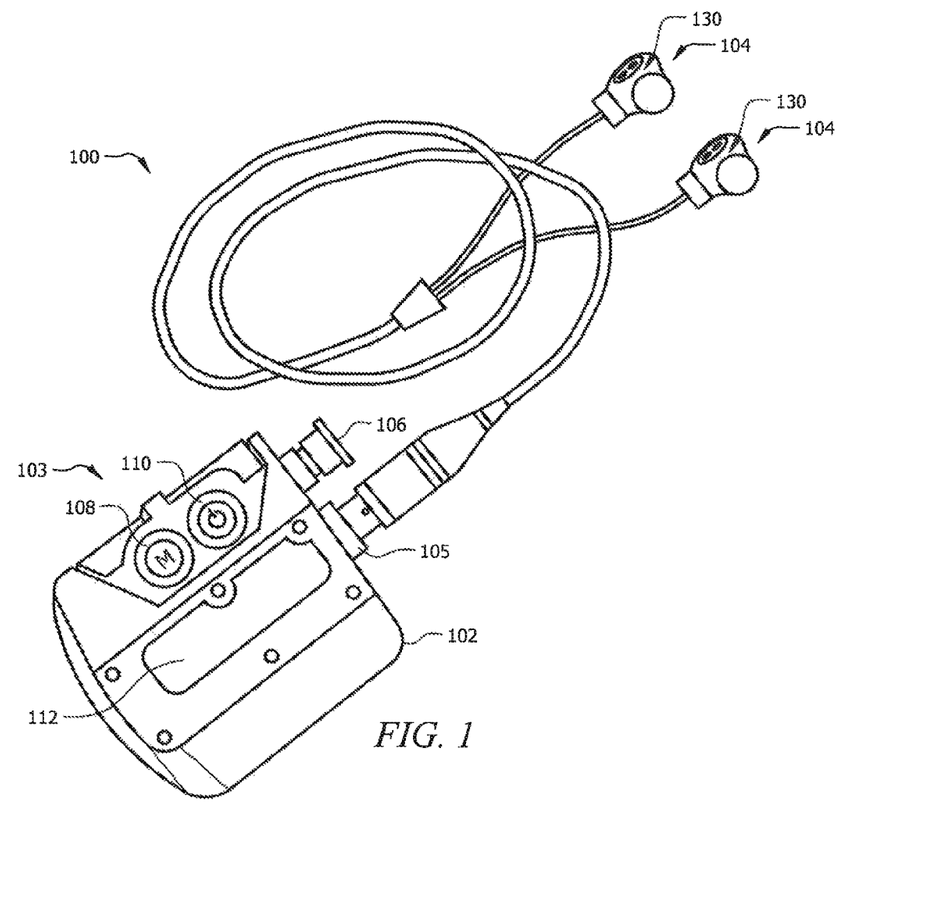
FIG. 1 illustrates an active hearing protection device according to an embodiment of the disclosure.

Referring now to FIG. 1, an exemplary embodiment of an active hearing protection device 100 is shown. The active hearing protection device 100 may comprise a set of earmuffs 104 (which may also be known as earbuds, headphones, or a similar name), wherein the earmuffs 104 are connected to a communication device 102. The communication device 102 may comprise a user interface 103 operable to receive input from a user and communicate information to the user. In some embodiments, the user interface 103 may comprise a menu button 108, a power button 110 and a screen 112. In some embodiments the communication device 102 may comprise one or more ports 105 and 106 for connecting earmuffs 104, radio devices, microphones, or other devices to the communication device 102. In some embodiments, the communication device 102 and earmuffs 104 may provide active hearing protection to a wearer (or user), as would be understood by those skilled in the art. Additionally, the communication device 102 may receive data related to active hearing protection from the earmuffs 104, such as noise exposure levels.

In some embodiments, the earmuffs 104 may communicate sounds to a user, such as voice communication via a radio connection. Additionally, the earmuffs 104 may comprise a voice pick-up device, which may pick up the voice of a wearer for communication over the radio connection. Alternatively, the communication device 102 may connect to an external microphone for picking up the voice of the wearer. This may be useful if the communication device 102 is operating as (or connected to) a radio device.

When a user is wearing the active hearing protection device 100, a fit test may be performed when the device 100 is powered on, to ensure that the earmuffs 104 are worn correctly and providing adequate hearing protection. The fit test may occur automatically when the device is powered on, to ensure that the device is not used incorrectly. Additionally, while the device 100 is powered on, data may be collected about the conditions the user is experiencing, such as sound exposure, frequency levels, decibel levels, time of exposure, etc.

In some embodiments, the earmuffs 104 may be designed to allow for automatic powering on or off of the communication device 102. For example, the earmuffs 104 may comprise an indicator mechanism 130 for determining if the earmuffs 104 are inserted into a user's ears. When it is determined that both earmuffs 104 are inserted into the user's ears, the device 102 may be powered on, and when it is determined that at least one of the earmuffs 104 is not inserted into the user's ear(s), the device may be automatically powered off. In some embodiments, the indication mechanism may comprise one of the following: a pressure sensor, a push button, a thermal sensor, and/or an accelerometer (or other movement sensor).

Figure 2:
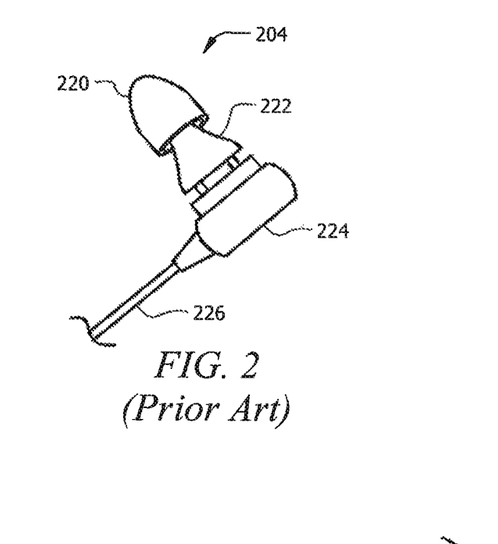
FIG. 2 illustrates a typical earmuff used with an active hearing protection device.

Referring now to FIG. 2, a typical earmuff 204 is shown, wherein the earmuff 204 is designed for use with an active hearing protection device 100 (shown in FIG. 1). The earmuff 204 comprises an internal portion 220 that fits into the ear canal of a user, a external portion 224 that remains outside the ear canal of a user when the earmuffs 204 is worn, and a connector 222 between the internal portion 220 and external portion 224. The external portion 224 may connect to a cord 226, wherein the cord 226 may connect to a device 102 (as shown in FIG. 1). The earmuff 204 may comprise a speaker for communication purposes and/or active noise protection (or active noise cancellation) purposes. In some embodiments, the earmuff 204 may comprise a microphone and/or voice pick-up device for communication purposes.

Figure 3A:
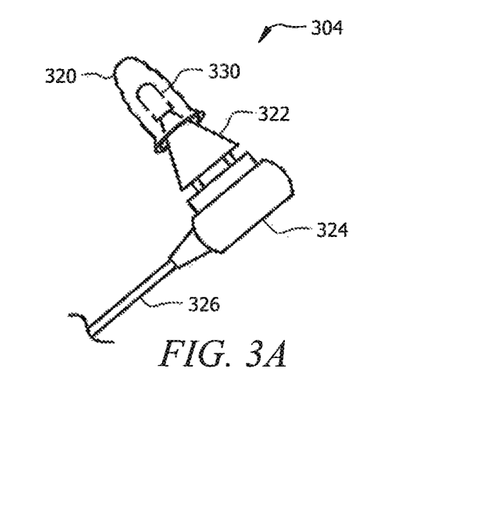
FIGS. 3A-3B illustrate an earmuff comprising an indicator mechanism used with an active hearing protection device according to an embodiment of the disclosure.
Figure 3B:
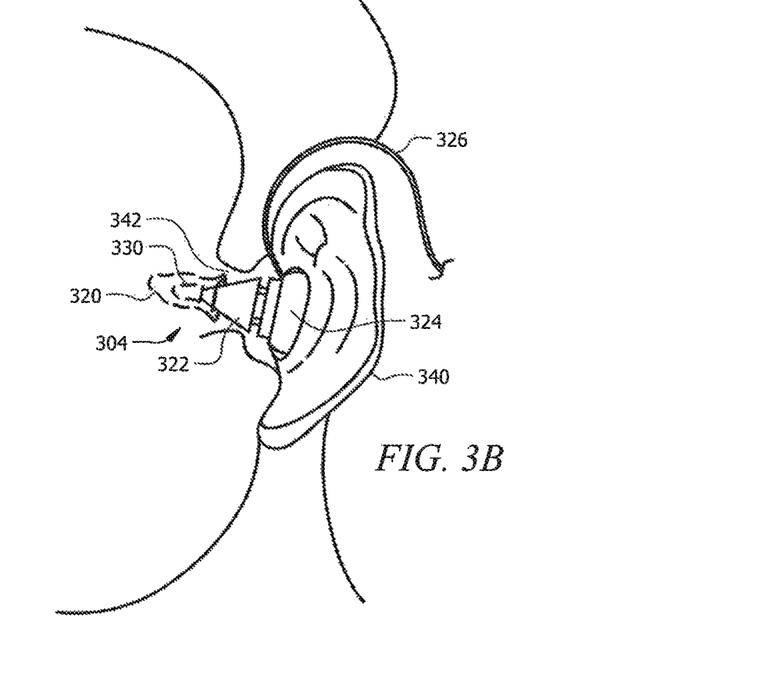

Referring now to FIGS. 3A-3B, an exemplary embodiment of an earmuff 304 is shown. The earmuff 304 may comprise an internal portion 320, an external portion 324, a connector 322, and cord 326. In some embodiments, the earmuff 304 may comprise an indicator mechanism (as described in FIG. 1) for determining if the earmuff 304 is inserted into a user's ears 340. In the embodiment of FIGS. 3A-3B, the indicator mechanism may comprise a pressure cell 330 located within the earmuff 304. The pressure cell 330 may be used to automatically power on and power off an active hearing protection device (as described in FIG. 1). The pressure cell 330 may be located within the internal portion 320 of the earmuff 304, and may therefore be compressed when the internal portion 320 is inserted into a user's ear 340, as shown in FIG. 3B. A predetermined level of compression of the pressure cell 330 may indicate (to a communication device) that the earmuff 304 is inserted into the ear canal 342 of a user. Additionally, if the pressure cell 330 is not compressed to the predetermined level, this may indicate that the earmuff 304 is not inserted into the ear canal 342 of the user.

Figure 4A:
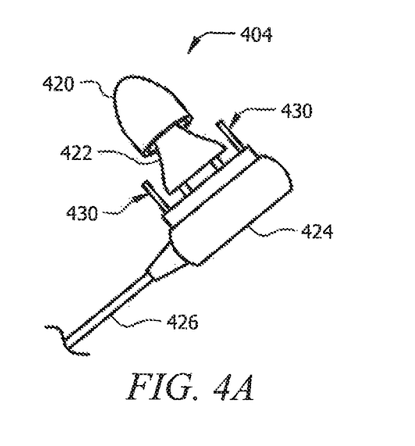
FIGS. 4A-4B illustrate another earmuff comprising an indicator mechanism used with an active hearing protection device according to an embodiment of the disclosure.
Figure 4B:
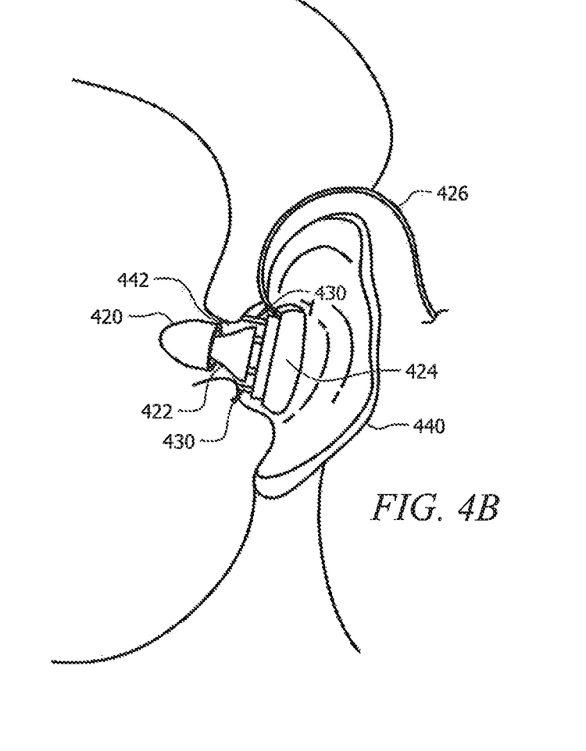

Referring now to FIGS. 4A-4B, an alternative embodiment of an earmuff 404 is shown. The earmuff 404 may comprise an internal portion 420, an external portion 424, a connector 422, and cord 426. In some embodiments, the earmuff 404 may comprise an indicator mechanism (as described in FIG. 1) for determining if the earmuff 404 is inserted into a user's ears 440. In the embodiment of FIGS. 4A-4B, the indicator mechanism may comprise one or more push buttons 430 located within the earmuff 404. The push buttons 430 may be used to automatically power on and power off an active hearing protection device (as described in FIG. 1). In some embodiments, the push buttons 430 may be located between the internal portion 420 and external portion 424 of the earmuff 404. In some embodiments, the push buttons 430 may be positioned on the earmuff 404 such that, when the internal portion 420 of the earmuff 404 is inserted into the ear canal 442 of a user, the push buttons 430 may contact the surface of the ear canal 442, as shown in FIG. 4B. A predetermined level of compression of the push buttons 430 may indicate (to a communication device) that the earmuff 404 is inserted into the ear canal 442 of a user. Additionally, if the push buttons 430 are not compressed to the predetermined level, this may indicate that the earmuff 404 is not inserted into the ear canal 442 of the user.

Figure 5A:
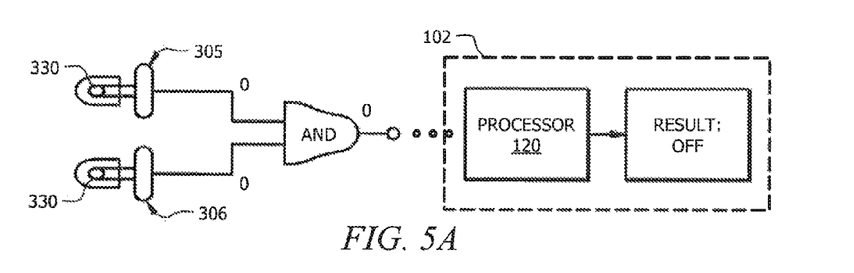
FIGS. 5A-5D illustrate a method for using an earmuff comprising an indicator mechanism.

Referring now to FIGS. 5A-5D, a method for turning on and turning off a communication device 102 of an active hearing protection device 100 (as described in FIG. 1) is described. The earmuffs 305 and 306 may be similar to the earmuffs 304 described in FIGS. 3A-3B. In some embodiments, the communication device 102 may be constantly (or periodically) receiving information from the earmuffs 305 and 306. In FIG. 5A, the device 102 is not being worn by a user. The right earmuff 305 and the left earmuff 306, and the pressure cells 330 located in the earmuffs 305 and 306, are uncompressed and therefore both pressure cells 330 are indicating that the earmuffs 305 and 306 are not being worn. The communication device 102 may comprise a processor 120 operable to receive and process the information from the earmuffs 305 and 306. The processor 120 may determine from the information if the device 102 should be turned off or on. The processor may follow an AND condition to turn on the device 102, wherein the default if the AND condition is not met is to turn off the device 102.

Figure 5B:
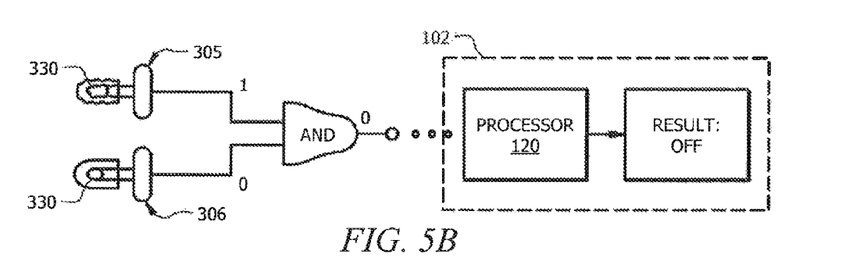

In FIG. 5B, the right earmuff 305 has been inserted into a user's ear, and the pressure cell 330 within the earmuff 305 is compressed. Therefore the right earmuff 305 is indicating to the processor 120 that is it inserted into a user's ear. However, the left earmuff 306 is not inserted into a user's ear, and the pressure cell 330 within the left earmuff 306 is not compressed. Therefore, the left earmuff 306 is indicating to the processor 120 that it is not inserted into a user's ear. Because the processor is following an AND condition to turn on the device 102, and the condition is not met, the device 102 may remain off. This scenario may occur when a user is in the process of inserting the earmuffs before use, or when the user is removing the earmuffs after use.

Figure 5C:
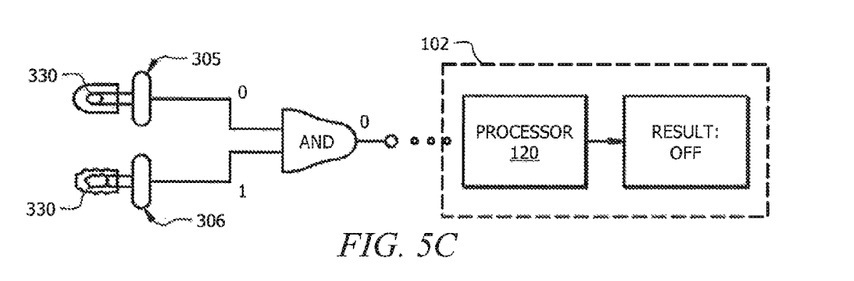

In FIG. 5C, the left earmuff 306 has been inserted into a user's ear, and the pressure cell 330 within the earmuff 306 is compressed. Therefore the left earmuff 306 is indicating to the processor 120 that is it inserted into a user's ear. However, the right earmuff 305 is not inserted into a user's ear, and the pressure cell 330 within the right earmuff 305 is not compressed. Therefore, the right earmuff 305 is indicating to the processor 120 that it is not inserted into a user's ear. Because the processor is following an AND condition to turn on the device 102, and the condition is not met, the device 102 may remain off. This scenario may occur when a user is in the process of inserting the earmuffs before use, or when the user is removing the earmuffs after use.

Figure 5D:
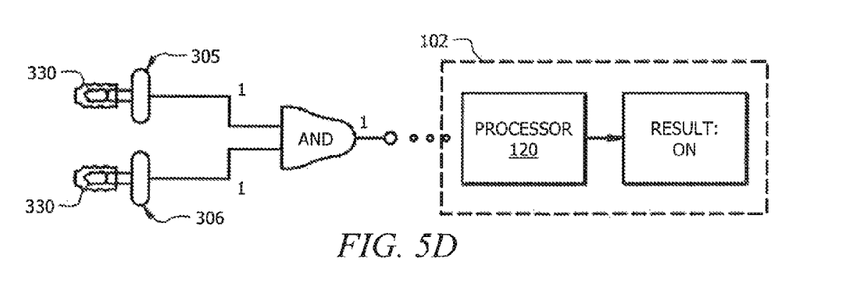

In FIG. 5D, the right earmuff 305 and the left earmuff 306 have been inserted into a user's ear. Both of the pressure cells 330 in the earmuffs 305 and 306 have been compressed and are therefore indicating to the processor 120 that the earmuffs 305 and 306 are inserted into the user's ears. Because the process is following an AND condition and the condition has been met, the processor 120 may indicate instructions to turn on the device 102. In some embodiments, the processor 120 may also indicated instructions for the device 102 to automatically complete a fit test once both earmuffs 305 and 306 are inserted into the user's ears.

In some embodiments, turning on the communication device 102 may comprise a delay (ten seconds, for example) which may allow for the earmuffs 305 and 306 to expand into the ear canal of the user. Therefore, when the fit test is completed, the earmuffs 305 and 306 may be completely fitted into the ear canal, providing an accurate fit test. However, turning off the device 102 may not comprise a delay, wherein the device 102 may be immediately turned off if the AND condition is not met. This may prevent the user reinserting the earmuff 305 or 306 without activating a new fit test. In other words, if an earmuff 305 or 306 is removed, the device 102 may be approximately immediately turned off. Then, when the earmuff 305 or 306 is reinserted by the user, the device 102 may be turned on and a new fit test may be initiated by the device 102.

Figure 6A:
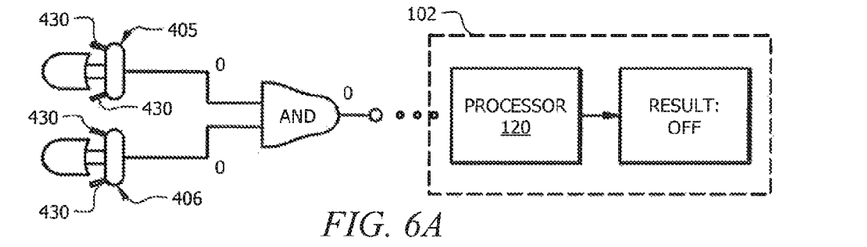
FIGS. 6A-6D illustrate another method for using an earmuff comprising an indicator mechanism.

Referring now to FIGS. 6A-6D, a method for turning on and turning off a communication device 102 of an active hearing device 100 is described. The earmuffs 405 and 406 may be similar to the earmuffs 404 described in FIGS. 4A-4B. In some embodiments, the communication device 102 may be constantly (or periodically) receiving information from the earmuffs 405 and 406. In FIG. 6A, the device 102 is not being worn by a user. The right earmuff 405 and the left earmuff 406, and the push buttons 430 located on the earmuffs 405 and 406, are uncompressed and therefore both push buttons 430 are indicating that the earmuffs 405 and 406 are not being worn. The communication device 102 may comprise a processor 120 operable to receive and process the information from the earmuffs 405 and 406. The processor 120 may determine from the information if the device 102 should be turned off or on. The processor may follow an AND condition to turn on the device 102, wherein the default if the AND condition is not met is to turn off the device 102.

Figure 6B:
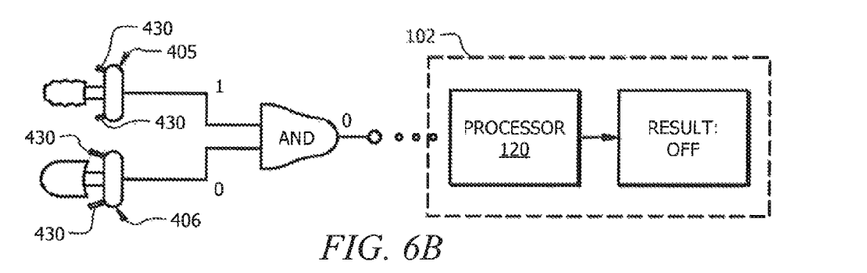

In FIG. 6B, the right earmuff 405 has been inserted into a user's ear, and the push button 430 of the right earmuff 405 is compressed. Therefore the right earmuff 405 is indicating to the processor 120 that is it inserted into a user's ear. However, the left earmuff 406 is not inserted into a user's ear, and the push button 430 of the left earmuff 406 is not compressed. Therefore, the left earmuff 406 is indicating to the processor 120 that it is not inserted into a user's ear. Because the processor is following an AND condition to turn on the device 102, and the condition is not met, the device 102 may remain off. This scenario may occur when a user is in the process of inserting the earmuffs before use, or when the user is removing the earmuffs after use.

Figure 6C:
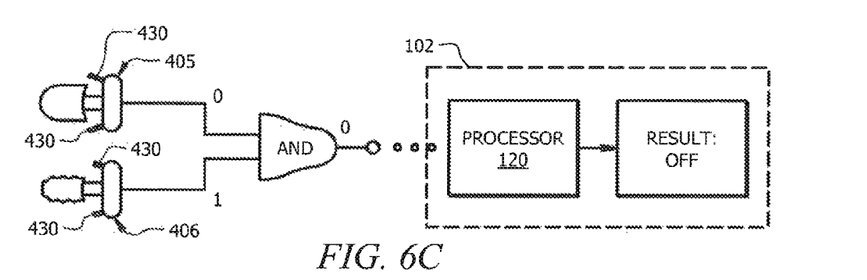

In FIG. 6C, the left earmuff 406 has been inserted into a user's ear, and the push button 430 of the left earmuff 406 is compressed. Therefore the left earmuff 406 is indicating to the processor 120 that is it inserted into a user's ear. However, the right earmuff 405 is not inserted into a user's ear, and the push button 430 of the right earmuff 405 is not compressed. Therefore, the right earmuff 405 is indicating to the processor 120 that it is not inserted into a user's ear. Because the processor is following an AND condition to turn on the device 102, and the condition is not met, the device 102 may remain off. This scenario may occur when a user is in the process of inserting the earmuffs before use, or when the user is removing the earmuffs after use.

Figure 6D:
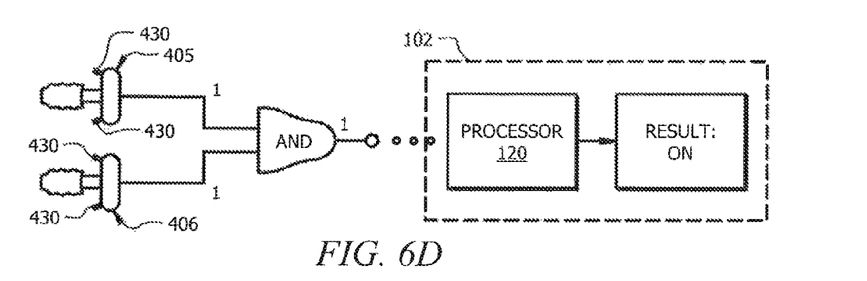

In FIG. 6D, the right earmuff 405 and the left earmuff 406 have been inserted into a user's ear. Both of the push buttons 430 on the earmuffs 405 and 406 have been compressed and are therefore indicating to the processor 120 that the earmuffs 405 and 406 are inserted into the user's ears. Because the process is following an AND condition and the condition has been met, the processor 120 may indicate instructions to turn on the device 102. In some embodiments, the processor 120 may also indicated instructions for the device 102 to automatically complete a fit test once both earmuffs 405 and 406 are inserted into the user's ears.

In some embodiments, turning on the communication device 102 may comprise a delay (ten seconds, for example) which may allow for the earmuffs 405 and 406 to expand into the ear canal of the user. Therefore, when the fit test is completed, the earmuffs 405 and 406 may be completely fitted into the ear canal, providing an accurate fit test. However, turning off the device 102 may not comprise a delay, wherein the device 102 may be immediately turned off if the AND condition is not met. This may prevent the user reinserting the earmuff 405 or 406 without activating a new fit test. In other words, if an earmuff 405 or 406 is removed, the device 102 may be approximately immediately turned off. Then, when the earmuff 405 or 406 is reinserted by the user, the device 102 may be turned on and a new fit test may be initiated by the device 102.

Some embodiments of the disclosure may comprise additional methods for automatically powering on or off an active hearing protection device. One method may comprise receiving, by a processor in the active hearing protection device, information from two earmuffs, wherein the earmuffs are connected to the active hearing protection device; receiving indication from a first indicator mechanism that a first earmuff has been inserted into a user's ear, receiving indication from a second indicator mechanism that a second earmuff has been inserted into a user's ear; powering on the active hearing protection device, after receiving indication from both the first indicator and the second indicator that both the first earmuff and the second earmuff have been inserted into a user's ear, performing a fit test on the first earmuff and the second earmuff after a delay; and receiving noise exposure data from the earmuffs while the active hearing protection device is turned on.

In some embodiments, the method may further comprise receiving indication from the first indicator mechanism that the first earmuff has been removed from a user's ear, and powering off the active hearing protection device. In some embodiments, the method may further comprise receiving indication from the first indicator mechanism that the first earmuff has been reinserted into a user's ear; powering on the active hearing protection device; performing a fit test on the first earmuff and the second earmuff after a delay; and receiving noise exposure data from the earmuffs while the active hearing protection device is turned on. In some embodiments, the method may further comprise receiving indication from the second indicator mechanism that the second earmuff has been removed from a user's ear; and powering off the active hearing protection device. In some embodiments, the method may further comprise receiving indication from the second indicator mechanism that the second earmuff has been reinserted into a user's ear; powering on the active hearing protection device; performing a fit test on the first earmuff and the second earmuff after a delay; and receiving noise exposure data from the earmuffs while the active hearing protection device is turned on.

In some embodiments, the indication mechanism comprises a pressure sensor located within an internal portion of the earmuff, and wherein the pressure sensor is compressed when the internal portion of the earmuff is inserted into a wearer's ear canal. In some embodiments, the indication mechanism comprises a push button operable to interact with the surface of a wearer's ear canal.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. An active hearing protection device comprising:
   a communication device configured to provide active hearing protection to a wearer;
   a set of earmuffs connected to the communication device, wherein each earmuff comprises an indicator mechanism configured to indicate to the communication device when the earmuff is inserted into a user's ear;
   a processor configured to receive information from the set of earmuffs and the indicator mechanisms of the earmuffs and configured to automatically power the active hearing protection device on or off based on the information received from the indicator mechanism(s), wherein the information is related to whether the earmuffs are inserted into a user's ears;
   wherein the active hearing protection device is configured to perform a fit test each time the processor powers the active hearing protection device on based on the information received from the indicator mechanism(s), after a delay that allows each earmuff to expand into an ear canal of the wearer, to ensure that the earmuffs are worn correctly and providing adequate hearing protection.

2. The device of claim 1, wherein, when it is determined that both earmuffs are inserted into the user's ears, the active hearing protection device is powered on, and when it is determined that at least one of the earmuffs is not inserted into the user's ear(s), the active hearing protection device is powered off.

3. The device of claim 1, wherein the communication device comprises:
a user interface configured to receive input from a user and communicate information to the user, the user interface comprises a menu button, a power button and a screen; and
one or more ports for connecting the earmuffs, radio devices, microphones, and other devices to the communication device.

4. The device of claim 1, wherein the information received by the communication device from the earmuffs comprises data related to active hearing protection from the earmuffs, including one or more of the following: noise exposure levels, frequency levels, decibel levels, and time of exposure.

5. The device of claim 1, wherein the earmuffs are configured to communicate voice communication to a user received via a radio connection, and wherein the earmuffs may comprise a voice pick-up device configured to pick up the voice of a wearer for communication over the radio connection.

6. The device of claim 1, wherein the delay causes the fit test to be completed at least 10 seconds after the device is turned on.

7. The device of claim 1, wherein the indication mechanism(s) comprise one or more of the following: a pressure sensor, a push button, a thermal sensor, and an accelerometer.

8. The device of claim 1, wherein the indication mechanism comprises a pressure sensor located within an internal portion of the earmuff, and wherein the pressure sensor is compressed when the internal portion of the earmuff is inserted into a wearer's ear canal.

9. The device of claim 1, wherein the indication mechanism comprises a push button configured to interact with the surface of a wearer's ear canal.

10. An active hearing protection device comprising:
a communication device configured to provide active hearing protection to a wearer;
a set of earmuffs connected to the communication device, wherein each earmuff comprises an indicator mechanism configured to indicate to the communication device when the earmuff is inserted into a user's ear;
a processor configured to receive information from the set of earmuffs and the indicator mechanisms of the earmuffs and configured to automatically power the active hearing protection device on or off based on the information received from the indicator mechanism(s), wherein the information is related to whether the earmuffs are inserted into a user's ears;
wherein:
when it is determined that both earmuffs are inserted into the user's ears, the active hearing protection device is powered on, and when it is determined that at least one of the earmuffs is not inserted into the user's ear(s), the active hearing protection device is powered off;
the information received by the communication device from the earmuffs comprises noise exposure data related to active hearing protection from the earmuffs; and
a fit test is performed by the active hearing protection device each time the processor powers the active hearing protection device on based on the information received from the indicator mechanism(s), after a delay that allows each earmuff to expand into an ear canal of the wearer to ensure that the earmuffs are worn correctly and providing adequate hearing protection.

11. The device of claim 10, wherein the indication mechanism comprises a pressure sensor located within an internal portion of the earmuff, and wherein the pressure sensor is compressed when the internal portion of the earmuff is inserted into a wearer's ear canal.

12. The device of claim 10, wherein the indication mechanism comprises a push button configured to interact with the surface of a wearer's ear canal.

13. The device of claim 10, wherein the delay causes the fit test to be completed at least 10 seconds after the device is turned on.

14. The device of claim 10, wherein turning off the active hearing protection device happens approximately immediately when at least one indicator mechanism indicates that at least one earmuff has been removed from the ear of a wearer.

15. A method for automatically powering on or off an active hearing protection device comprising:
receiving, by a processor in the active hearing protection device, information from two earmuffs, wherein the earmuffs are connected to the active hearing protection device;
receiving indication from a first indicator mechanism that a first earmuff has been inserted into a user's ear;
receiving indication from a second indicator mechanism that a second earmuff has been inserted into a user's ear;
powering on the active hearing protection device, after receiving indication from both the first indicator and the second indicator that both the first earmuff and the second earmuff have been inserted into a user's ear;
performing a fit test on the first earmuff and the second earmuff after a delay each time the active hearing protection device is powered on in response to receiving the indication from both the first indicator and the second indicator that both the first earmuff and the second earmuff have been inserted into a user's ears; and
receiving noise exposure data from the earmuffs while the active hearing protection device is turned on.

16. The method of claim 15 further comprising:
receiving indication from the first indicator mechanism that the first earmuff has been removed from a user's ear; and
powering off the active hearing protection device.

17. The method of claim 16 further comprising:
receiving indication from the first indicator mechanism that the first earmuff has been reinserted into a user's ear;
powering on the active hearing protection device;
performing a fit test on the first earmuff and the second earmuff after a delay; and
receiving noise exposure data from the earmuffs while the active hearing protection device is turned on.

18. The method of claim 15 further comprising:
receiving indication from the second indicator mechanism that the second earmuff has been removed from a user's ear; and
powering off the active hearing protection device.

19. The method of claim 15, wherein the indication mechanism comprises a pressure sensor located within an internal portion of the earmuff, and wherein the pressure sensor is compressed when the internal portion of the earmuff is inserted into a wearer's ear canal.

20. The method of claim 15, wherein the indication mechanism comprises a push button configured to interact with the surface of a wearer's ear canal The present application, filed on or after Mar. 16, 2013, is being examined under the first inventor to file provisions of the AIA.

* * * * *

UNITED STATES PATENT AND TRADEMARK OFFICE
CERTIFICATE OF CORRECTION

PATENT NO. : 9,949,878 B2
APPLICATION NO. : 14/645114
DATED : April 24, 2018
INVENTOR(S) : Sunil Bhila Pawar and Trym Holter It is certified that error appears in the above-identified patent and that said Letters Patent is hereby corrected as shown below:

In the Claims

Column 12, Line 64 Claim 20: delete "The present application, filed on or after Mar. 16, 2013, is being examined under the first inventor to file provisions of the AIA"

Signed and Sealed this
Twenty-first Day of August, 2018

Andrei Iancu
*Director of the United States Patent and Trademark Office*